(12) United States Patent
Ravishankar et al.

(10) Patent No.: US 12,106,838 B2
(45) Date of Patent: Oct. 1, 2024

(54) SYSTEMS AND METHODS FOR RESPIRATORY SUPPORT RECOMMENDATIONS

(71) Applicant: GE Precision Healthcare LLC, Milwaukee, WI (US)

(72) Inventors: Hariharan Ravishankar, Karnataka (IN); Abhijit Patil, Karnataka (IN); Rohit Pardasani, Karnataka (IN)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 593 days.

(21) Appl. No.: 17/362,612

(22) Filed: Jun. 29, 2021

(65) Prior Publication Data

US 2021/0407648 A1    Dec. 30, 2021

(30) Foreign Application Priority Data

Jun. 29, 2020    (IN) .............................. 202041027500

(51) Int. Cl.
*G06Q 10/00*    (2023.01)
*G16H 20/30*    (2018.01)
*G16H 20/40*    (2018.01)
*G16H 30/40*    (2018.01)

(52) U.S. Cl.
CPC ............. *G16H 20/30* (2018.01); *G16H 20/40* (2018.01); *G16H 30/40* (2018.01)

(58) Field of Classification Search
CPC ......... G16H 20/30; G16H 20/40; G16H 30/40
See application file for complete search history.

(56) References Cited

U.S. PATENT DOCUMENTS

| 10,130,308 | B2 | 11/2018 | Tsvieli et al. |
| 11,087,464 | B2* | 8/2021 | Wagner .................... A61B 6/46 |
| 2010/0083968 | A1* | 4/2010 | Wondka ................. G16H 20/40 |
| | | | 128/204.23 |
| 2018/0137244 | A1 | 5/2018 | Sorenson et al. |
| 2019/0304606 | A1 | 10/2019 | Menon et al. |
| 2020/0126678 | A1 | 4/2020 | Douglas et al. |

(Continued)

FOREIGN PATENT DOCUMENTS

| IN | 202031019607 A | * | 6/2020 |
| JP | 2020515924 A | | 5/2020 |
| KR | 20200049503 A | | 5/2020 |

OTHER PUBLICATIONS

Pepe, P. et al., "Early Prediction of the Adult Respiratory Distress Syndrome by a Simple Method," Annals of Emergency Medicine, vol. 12, No. 12, Dec. 1983, 7 pages.

(Continued)

*Primary Examiner* — Rajesh Khattar
(74) *Attorney, Agent, or Firm* — McCoy Russell LLP

(57) ABSTRACT

Methods and systems are provided for generating respiratory support recommendations. In one embodiment, a method includes extracting imaging features from patient imaging information for a patient, extracting non-imaging features from patient clinical data of the patient, entering the imaging features and the non-imaging features to a joint model trained to output respiratory support recommendations as a function of the imaging features and the non-imaging features, and displaying one or more respiratory support recommendations output by the joint model.

13 Claims, 6 Drawing Sheets

(56) References Cited

U.S. PATENT DOCUMENTS

| | | | |
|---|---|---|---|
| 2020/0152330 A1 | 5/2020 | Anushiravani et al. | |
| 2020/0373018 A1* | 11/2020 | Segal | G16H 50/70 |
| 2020/0410666 A1* | 12/2020 | Wagner | G06N 3/08 |
| 2021/0142910 A1* | 5/2021 | Hafez | G06N 5/01 |

OTHER PUBLICATIONS

"Pneumonia severity index," Wikipedia Website, Available Online at https://en.wikipedia.org/wiki/Pneumonia_severity_index, Aug. 15, 2005, 5 pages.

Ennett, C, et al., "Predicting Respiratory Instability in the ICU," Proceedings of the 30th Annual International IEEE EMBS Conference, Aug. 20, 2008, Vancouver, British Columbia, Canada, 4 pages.

Laher, A. et al., "Mechanically Ventilating the Severe Asthmatic," Journal of Intensive Care Medicine, vol. 33, No. 9, Available Online Nov. 5, 2017, Sep. 2018, 11 pages.

Cardenas, Y. et al., "Respiratory Support Strategies and Nonconventional Ventilation Modes in Oncologic Critical Care," Oncological Critical Care, Springer Nature Switzerland AG, Jan. 10, 2019, 10 pages.

Jiang, X. et al., "Towards an Artificial Intelligence Framework for Data-Driven Prediction of Coronavirus Clinical Severity," Computers, Materials & Continua, vol. 63, No. 1, Mar. 2020, 15 pages.

Wang, Y. et al., "Temporal Changes of CT Findings in 90 Patients with COVID-19 Pneumonia: A Longitudinal Study," Radiology, vol. 296, No. 2, Mar. 19, 2020, 9 pages.

Li, K. et al., "CT image visual quantitative evaluation and clinical classification of coronavirus disease (COVID-19)," European Radiology, vol. 30, No. 4, Mar. 25, 2020, 10 pages.

Möhlenkamp, S. et al., "Ventilation of COVID-19 patients in intensive care units," Herz, vol. 45, Apr. 20, 2020, 3 pages.

Rigatelli, G. et al., "Intubation and Ventilation amid COVID-19: Comment," Anesthesiology, vol. 133, No. 2, Available Online Apr. 21, 2020, Aug. 2020, 3 pages.

Mei, X. et al., "Artificial intelligence-enabled rapid diagnosis of patients with COVID-19," Nature Medicine, vol. 26, May 19, 2020, 14 pages.

Chen, H. et al., "Clinical and imaging features of COVID-19," Radiology of Infectious Diseases, vol. 7, No. 2, Jun. 2020, 8 pages.

Ito, R. et al., "A review on the use of artificial intelligence for medical imaging of the lungs of patients with coronavirus disease 2019," Diagnostic and Interventional Radiology, vol. 26, No. 5, Sep. 2020, 6 pages.

ISA Korean Intellectual Property Office, International Search Report and Written Opinion Issued in Application No. PCT/US2021/039679, Oct. 21, 2021, WIPO, 8 pages.

* cited by examiner

SYSTEMS AND METHODS FOR RESPIRATORY SUPPORT RECOMMENDATIONS

CROSS-REFERENCE TO RELATED APPLICATIONS

This application claims priority to Indian Patent Application No. 202041027500, titled "SYSTEMS AND METHODS FOR RESPIRATORY SUPPORT RECOMMENDATIONS," and filed Jun. 29, 2020. The entire contents of the above-cited application are hereby incorporated by reference for all purposes.

TECHNICAL FIELD

Embodiments of the subject matter disclosed herein relate to providing clinical recommendations, and more particularly to using machine learning/artificial intelligence based models to provide respiratory support mode recommendations.

BACKGROUND

Treatment of certain respiratory conditions may include respiratory support interventions, such as supplemental oxygen, non-invasive ventilation, or invasive ventilation. Breathing support may include additional oxygen supplied through a nasal cannula or other device, without positive pressure. Non-invasive ventilation may be breathing support, including positive pressure, administered through a face mask, nasal mask, or other mechanism without tracheal intubation. Invasive ventilation may be breathing support delivered to a patient's lungs via an endotracheal tube or a tracheostomy tube. When treating emerging conditions such as COVID-19, clinical decisions about which type of respiratory support to provide a patient, when to provide such respiratory support, and the parameters for the respiratory support may be based on little evidence, or based on treatment protocols for other conditions. Accordingly, without established practices, COVID-19 patients may be administered respiratory support too late, treated too aggressively, or may not be administered the proper type of respiratory support. For example, some patients may be placed on invasive ventilation when non-invasive ventilation may be equally beneficial, which may increase the likelihood that the patients will incur side effects. Further, during acute outbreaks of COVID-19, respiratory support resources may become scarce, and thus evidence-based decision making around when to intubate and when to extubate patients may free up these critical resources for patients exhibiting severe symptoms that necessitate invasive ventilation.

SUMMARY

The present disclosure at least partially addresses the issues described above. In one embodiment, the present disclosure provides a method including extracting imaging features from patient imaging information for a patient, extracting non-imaging features from patient clinical data of the patient, entering the imaging features and the non-imaging features to a joint model trained to output respiratory support recommendations as a function of the imaging features and the non-imaging features, and displaying one or more respiratory support recommendations output by the joint model.

The above advantages and other advantages and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which.

Figure 1:
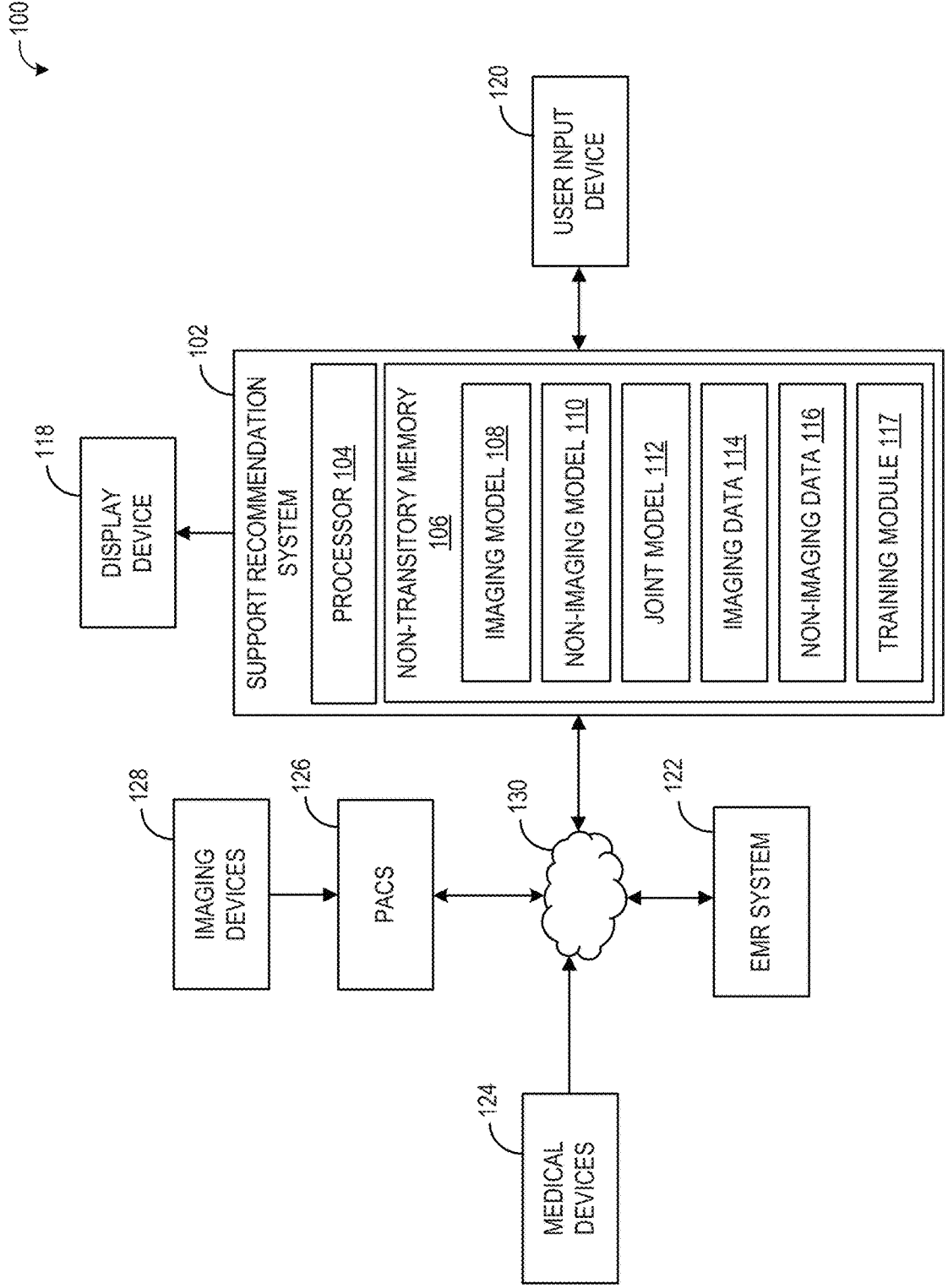
FIG. 1 schematically shows an example integrative longitudinal respiratory management system including a support recommendation system that may generate recommendations for administering respiratory support to patients based on both imaging data and non-imaging data, according to an embodiment of the disclosure.

The drawings illustrate specific aspects of the described systems and methods. Together with the following description, the drawings demonstrate and explain the structures, methods, and principles described herein. In the drawings, the size of components may be exaggerated or otherwise modified for clarity. Well-known structures, materials, or operations are not shown or described in detail to avoid obscuring aspects of the described components, systems and methods.

DETAILED DESCRIPTION

In COVID-19 positive subjects, timely intervention of mechanical ventilation (intubation) is key to successful recovery of the patients. Conversely, predicting timely weaning of the patient (extubation) is equally important to limit potential damage due to excessive mechanical ventilation. Additionally, given rising cases of COVID-19 and demand for ventilators, accurate prediction of ventilation requirements can help manage limited ventilator resources and help target care to the right patients. Also, in some cases non-invasive ventilation or conventional oxygen support may be sufficient. In such cases, predicting the need for non-invasive ventilation or oxygen support along with suggestive settings (e.g., oxygen fraction (FiO2) and positive end expiratory pressure (PEEP)) may be helpful.

Thus, embodiments are provided herein to address the challenge of continuously monitoring and predicting need for ventilation (invasive/non-invasive) or oxygen support for COVID-19 patients and patients for other types of respiratory conditions, such as bacterial pneumonia, influenza, acute respiratory distress syndrome, etc., using integrated artificial intelligence (AI-based methods and systems. The integrated AI-based approach described herein relies on two sets of biomarkers for disease state/progression-imaging biomarkers and non-imaging biomarkers. Imaging biomarkers include (but are not limited to) chest X-rays, computed tomography (CT) images, and ultrasound images. Non-imaging biomarkers include patient signals during the course of a hospital stay, e.g., vital signs, lab tests, haemodynamic tests, ventilation-related signals, and patient history information. Both the imaging biomarkers and non-imaging biomarkers may include information that can be used by the models described herein to evaluate patient condition and provide machine learning predictions of future respiratory support needs. For example, longitudinal imaging scans (e.g., where multiple scans are performed over time/as a patient is exhibiting COVID-19 or other types of respiratory conditions) may reveal patterns of worsening disease condition or recovery. This may include pleural line thickening, confluence of B-lines, and appearance of A-lines on lung ultrasound images during the recovery phase, for example.

The AI-based approach described herein may include multiple AI models that may evaluate the imaging biomarkers and non-imaging biomarkers separately and together in order to provide recommendations for respiratory support (e.g., whether or not a particular patient should be intubated for invasive ventilation) and, in some examples, machine settings for the recommended respiratory support. In this way, biomarkers from different cues (imaging and non-imaging) may be combined and used to continuously monitor, predict intubation, extubation, non-invasive ventilation events, or oxygen support requirements for COVID-19 patients.

FIG. 1 schematically shows an example integrative longitudinal respiratory management system 100 that may be implemented in a medical facility such as a hospital. System 100 may include a support recommendation system 102. Support recommendation system 102 may include resources (e.g., processor(s) 104 and non-transitory memory 106) allocated to receive respiratory monitoring data for one or more patients (including imaging data and non-imaging data), enter the patient respiratory data as input to one or more respiration support models, and display the output of the one or more models, where the output may be used by clinicians to guide clinical decisions, including initiating, transitioning, and ceasing respiratory therapy such as invasive or non-invasive oxygen delivery. In some embodiments, the support recommendation system 102 is incorporated into one or more devices of a medical facility system, for example, a picture archive and communication system (PACS), a hospital operational system, a respiratory therapy device or other medical device, or an imaging device. In some embodiments, the support recommendation system 102 is disposed at a device (e.g., edge device, server, etc.) communicably coupled to various medical facility devices and systems via wired and/or wireless connections. In some embodiments, the support recommendation system 102 is disposed at a separate device (e.g., a workstation) which can receive clinical data and images from the various medical facility devices and systems. The support recommendation system 102 may be coupled to a user input device 120 and a display device 118.

Support recommendation system 102 includes a processor 104 configured to execute machine readable instructions stored in non-transitory memory 106. Processor 104 may be single core or multi-core, and the programs executed thereon may be configured for parallel or distributed processing. In some embodiments, the processor 104 may optionally include individual components that are distributed throughout two or more devices, which may be remotely located and/or configured for coordinated processing. In some embodiments, one or more aspects of the processor 104 may be virtualized and executed by remotely-accessible networked computing devices configured in a cloud computing configuration.

Non-transitory memory 106 may store an imaging model 108, a non-imaging model 110, a joint model 112, imaging data 114, and non-imaging data 116. Imaging model 108 may be configured to receive imaging information/imaging features (which may be saved as part of imaging data 114) from one or more medical images (e.g., ultrasound images, computed tomography images, magnetic resonance images, etc.) as input and output one or more respiratory support recommendations based on the input. As will be described in more detail below, the one or more respiratory support recommendations may include a recommended respiratory support mode for a patient (e.g., no support, oxygen support, non-invasive ventilation, or mechanical ventilation) and, in some examples where the recommended support mode includes some sort of respiratory support, recommended settings/parameters for the recommended support (e.g., recommended ventilator parameters).

Imaging model 108 may be a machine learning/artificial intelligence model, such as a decision tree or artificial neural network. Thus, imaging model 108 may include one or more decision trees, deep neural networks, or other models. When imaging model 108 includes a deep neural network, the deep neural network may comprise a plurality of parameters (including weights, biases, activation functions), and instructions for implementing the one or more deep neural networks to receive the imaging features and map the imaging features to output, wherein the output may include one or more respiratory support recommendations and/or output usable to determine one or more respiratory support recommendations (e.g., a numeric score). When imaging model 108 includes a decision tree, the decision tree may include a plurality of parameters and/or hyperparameters (including nodes, leaves, and the like), and instructions for implementing the one or more decision trees to receive the imaging features and map the imaging features to output. Imaging model 108 may include trained and/or untrained neural networks, decision trees, etc., and may further include various data, or metadata pertaining to the one or more neural networks stored therein.

Non-imaging model 110 may be configured to receive clinical information/non-imaging features (which may be saved as part of non-imaging data 116) from one or more patient monitoring devices, patient electronic medical records, laboratory services, etc., as input and output one or more respiratory support recommendations based on the input, as explained above for the imaging model 108.

Non-imaging model 110 may be a machine learning/artificial intelligence model, such as a decision tree or artificial neural network. Thus, non-imaging model 110 may include one or more decision trees, deep neural networks, or other models. When non-imaging model 110 includes a deep neural network, the deep neural network may comprise a plurality of parameters (including weights, biases, activation functions), and instructions for implementing the one or more deep neural networks to receive the non-imaging features and map the non-imaging features to output, wherein the output may include one or more respiratory support recommendations and/or output usable to determine one or more respiratory support recommendations (e.g., a numeric score). When non-imaging model 110 includes a decision tree, the decision tree may include a plurality of parameters and/or hyperparameters (including nodes, leaves, and the like), and instructions for implementing the one or more decision trees to receive the imaging features and map the imaging features to output. Non-imaging model 110 may include trained and/or untrained neural networks, decision trees, etc., and may further include various data, or metadata pertaining to the one or more neural networks stored therein.

Joint model 112 may be configured to receive combined/concatenated imaging features and non-imaging features as input from imaging model 108 and non-imaging model 110 respectively and output one or more respiratory support recommendations based on the input, as explained above for the imaging model 108 and the non-imaging model 110. Joint model 112 may be a machine learning/artificial intelligence model, such as a decision tree or artificial neural network. Thus, joint model 112 may include one or more decision trees, deep neural networks, or other models. When joint model 112 includes a deep neural network, the deep neural network may comprise a plurality of parameters (including weights, biases, activation functions), and instructions for implementing the one or more deep neural networks to receive the imaging and non-imaging features and map the imaging and non-imaging features to output, wherein the output may include one or more respiratory support recommendations and/or output usable to determine one or more respiratory support recommendations (e.g., a numeric score). When joint model 112 includes a decision tree, the decision tree may include a plurality of parameters and/or hyperparameters (including nodes, leaves, and the like), and instructions for implementing the one or more decision trees to receive the imaging features and map the imaging features to output. Joint model 112 may include trained and/or untrained neural networks, decision trees, etc., and may further include various data, or metadata pertaining to the one or more neural networks stored therein.

In some examples, non-transitory memory 106 may further store training module 117, which comprises instructions for training one or more of machine learning/AI models stored in imaging model 108, non-imaging model 110, and joint model 112. Training module 117 may include instructions that, when executed by processor 104, cause support recommendation system 102 to conduct supervised learning (e.g., training) of imaging model 108, non-imaging model 110, and/or joint model 112. In some embodiments, training module 117 includes instructions for implementing one or more gradient descent algorithms, applying one or more loss functions, and/or training routines, for use in adjusting parameters of one or more of the machine learning/AI models described herein. In some embodiments, training module 117 includes instructions for intelligently selecting training data pairs from imaging data 114, where the training data pairs comprise medical images of a patient and corresponding ground truth data for that patient (e.g., expert annotations of clinical findings as well as prior and subsequent respiratory support administered to the patient and outcomes of the patient). Imaging data 114 may include imaging data that may be selected for training eligibility by an external source (e.g., expert clinician, software, and the like) such that not all of imaging data 114 may be used for training by training module 117. In some embodiments, training module 117 includes instructions for intelligently selecting training data pairs from non-imaging data 116, where the training data pairs comprise clinical data of a patient and corresponding ground truth data for that patient (e.g., expert annotations of prior and subsequent respiratory support administered to the patient and outcomes of the patient). Non-imaging data 116 may include non-imaging data that may be selected for training eligibility by an external source (e.g., expert clinician, software, and the like) such that not all of non-imaging data 116 may be used for training by training module 117. Models may be trained on a plurality of metrics where the models make calculations, assessments, and the like from the data (imaging/non-imaging) in the training data pairs and training module 117 compares output from the models to the ground truth data for that training data pair. A threshold absolute value of error may be used for training the models such that if an absolute value between a model output and the corresponding ground truth data for a training data pair exceeds the threshold absolute value, the training module 117 may not label the model output as a success. In some embodiments, the training module 117 is not disposed at the support recommendation system 102.

Training of the imaging model 108, non-imaging model 110, and/or joint model 112 may include the use of pre-processed and then extracted imaging and non-imaging features (e.g., rather than raw data), as explained below with respect to FIGS. 3 and 4. To get a generic robust model, data augmentation based on physics and biology cues may be used to generate more samples. Further, if there is lack of annotation, self-supervised learning techniques may be used to generate labelled data.

Imaging model 108, non-imaging model 110, and joint model 112 may each be trained to provide respiratory support recommendations for patients having a given condition, such as COVID-19. Thus, each of imaging model 108, non-imaging model 110, and joint model 112 may be trained with training data specific to patients having a confirmed or suspected diagnosis of COVID-19. However, the models described herein may be trained to provide respiratory support recommendations for other types of respiratory conditions, such as bacterial pneumonia, influenza, acute respiratory distress syndrome, etc.

Non-transitory memory 106 further stores imaging data 114. Imaging data 114 includes, for example, magnetic resonance (MR) images captured from an MR imaging system, ultrasound images acquired by an ultrasound system, etc. Non-transitory memory 106 further stores non-imaging data 116, which may include patient clinical data such as patient monitoring data captured from medical devices (e.g., heart rate monitors, pulse oximeters, electrocardiograms), patient medical history captured from an electronic medical record (EMR) system, lab results captured from the EMR system or a laboratory service, etc.

In some embodiments, the non-transitory memory 106 may include components disposed at two or more devices, which may be remotely located and/or configured for coordinated processing. In some embodiments, one or more aspects of the non-transitory memory 106 may include remotely-accessible networked storage devices configured in a cloud computing configuration.

User input device 120 may comprise one or more of a touchscreen, a keyboard, a mouse, a trackpad, a motion sensing camera, or other device configured to enable a user to interact with and manipulate data within support recommendation system 102. As an example, user input device 120 may enable a user to make a selection of patient imaging and non-imaging data to enter into imaging model 108, non-imaging model, and/or joint model 112 in order to be provided one or more recommendations for respiratory support for a patient.

Display device 118 may include one or more display devices utilizing virtually any type of technology. In some embodiments, display device 118 may comprise a computer monitor, and may display the one or more respiratory support recommendations described herein. Display device 118 may be combined with processor 104, non-transitory memory 106, and/or user input device 120 in a shared enclosure, or may be peripheral display devices and may comprise a monitor, touchscreen, projector, or other display device known in the art, which may enable a user to view respiratory support recommendations and/or interact with various data stored in non-transitory memory 106.

The support recommendation system 102 is communicatively connected to at least one network 130. Such communicative connections as well as the network itself may include, but are not limited to, a wide area network (WAN); a local area network (LAN); the internet; wired or wireless (e.g. optical, Bluetooth, radio frequency (RF) network; a cloud-based computer infrastructure of computers, routers, servers, gateways, etc.; or any combination thereof associated therewith that allows the system or portions thereof to communicate with one or more computing devices.

The network 130 may exemplarily be a network associated with a portion of a medical facility, for example an intensive care unit or department of a hospital, or may be more broadly located across medical devices of an entire hospital. It further will be recognized that while some embodiments and implementations of the systems and methods as disclosed herein may seek to operate on a single hospital or unit of a hospital, still other embodiments may connect a plurality of hospital networks, including hospitals currently owned or operated or otherwise affiliated with one another. In still further embodiments, while individual hospitals or groups of hospitals may use the support recommendation system 102, the support recommendation system 102 may receive and process information from a plurality of hospital networks including those unaffiliated with one another at the same time.

As depicted in FIG. 1, system 100 includes a plurality of medical devices 124. The medical devices 124 may include physiological monitoring devices as well as patient therapy devices. Physiological monitoring devices may include, but are not limited to, heart rate monitors, blood pressure oxygenation monitors, respiration monitors, electrocardiogram (ECG) monitors, electroencephalogram (EEG) monitors, or electromyography (EMG) monitors. Patient therapy devices may include, but are not limited to, mechanical ventilators, including invasive ventilators and non-invasive ventilation devices (e.g., positive pressure ventilators), and oxygen support devices (e.g., nasal cannulas delivering oxygen from a suitable supply). However, it will be recognized that therapy devices may also include capabilities to not only deliver patient therapy, but also to measure physiological parameters of a patient. For example, embodiments of the ventilators described herein may include gas analysis modules operable to measure gas concentrations expired by the patient.

The plurality of medical devices 124 may send patient clinical data to support recommendation system 102 via network 130. The data streams of patient clinical data (e.g., machine data, monitored patient physiological parameter data) are available in a time series format as acquired from the medical devices and may include, but are not limited to, time series information of alarms, device status, device settings, messages, and measured data. The time series data from the medical devices may be in waveform or binary format, audio data, image data, and/or video data.

System 100 includes a plurality of imaging devices 128. The plurality of imaging devices may include, but are not limited to, magnetic resonance imaging (MRI) devices, computed tomography (CT) devices, positron emission tomography (PET) devices, X-ray devices (including digital mammography devices, fluoroscopy devices, interventional devices, etc.), ultrasound devices, single-photon emission computerized tomography (SPECT) devices, and/or combinations thereof. Still further examples of imaging devices may include video and/or audio recording devices. The plurality of imaging devices 128 may be coupled to a picture archiving and communication system (PACS) 126. Each imaging device may be configured to acquire medical images of a patient and send the acquired images to PACS 126 for long-term storage. PACS 126 may store the images and, when requested, may retrieve one or more images and send the retrieved images to one or more connected devices, such as support recommendation system 102 which is coupled to PACS 126 via network 130. While FIG. 1 shows support recommendation system 102 communicatively coupled to PACS 126 and the imaging devices 128 communicatively coupled to PACS 126, in some examples, one or more of the imaging devices 128 may be directly communicatively coupled to support recommendation system 102 (via network 130).

Support recommendation system 102 is further coupled to an EMR system 122 via network 130. EMR system 122 may be an external database via a secured hospital interface, or EMR system 122 may be a local database (e.g., housed on a device of the medical facility). EMR system 122 may be a database stored in a mass storage device configured to communicate with secure channels (e.g., HTTPS and TLS), and store data in encrypted form. Further, the EMR system 122 is configured to control access to patient electronic medical records such that only authorized healthcare providers may edit and access the electronic medical records. An EMR for a patient may include patient demographic information, family medical history, past medical history, lifestyle information, preexisting medical conditions, current medications, allergies, surgical history, past medical screenings and procedures, past hospitalizations and visits, etc.

It should be understood that system 100 shown in FIG. 1 is for illustration, not for limitation. Another system may include more, fewer, or different components. One or more of the devices described herein may be implemented over a cloud or other computer network. For example, support recommendation system 102 and PACS 126 are shown in FIG. 1 as each constituting a single entity, but it is to be understood that support recommendation system 102 and/or PACS 126 may be distributed across multiple devices, such as across multiple servers.

Figure 2:
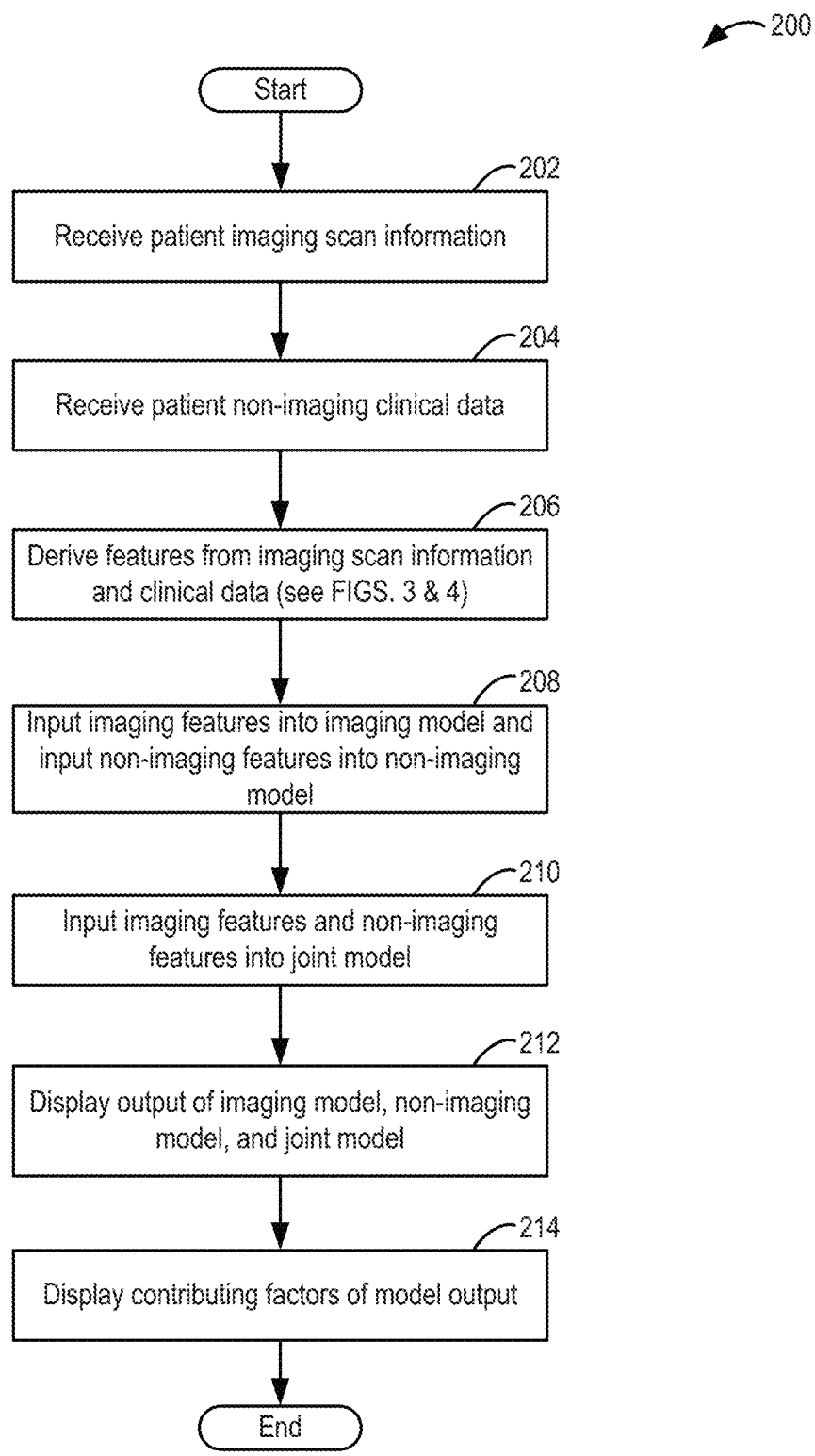
FIG. 2 is a flowchart illustrating a method for generating respiratory support recommendations via the support recommendation system of FIG. 1, according to an embodiment of the disclosure.

Referring to FIG. 2, a flow chart of a method 200 for generating respiratory support recommendations for a patient having COVID-19 is shown, according to an embodiment. Method 200 may be implemented by the support recommendation system 102, according to instructions stored in non-transitory memory 106 executed by processor 104. Method 200 is described with respect to the systems and devices of system 100 of FIG. 1, but it is to be understood that method 200 could be carried out with other systems and devices without departing from the scope of this disclosure. Method 200 may be executed in response to a request (e.g., entered by a user via a user input device, such as user input device 120) to generate respiratory support recommendations for a particular patient. In other examples, method 200 may be executed automatically as new data is received for the particular patient, or method 200 may be executed automatically at a predetermined frequency (e.g., once an hour, once a day, etc.). While method 200 is described with respect to a patient having a confirmed or suspected case of COVID-19, in some examples method 200 may be performed to generate respiratory support recommendations for patients having other conditions, such as influenza or other types of pneumonia.

At 202, patient imaging scan information is received. The patient imaging scan information may include medical images of the patient, findings of the medical images (which may be included as annotations on the images or as part of a report associated with the images), and other information associated with the medical images (e.g., metadata such as the date the image was acquired). The patient imaging scan information may be received from a PACS (e.g., PACS 126) and/or from one or more imaging devices (e.g., one or more imaging devices of the plurality of imaging devices 128). The patient imaging scan information may be stored, at least temporarily, on the support recommendation system (e.g., as part of imaging data 114).

At 204, patient non-imaging clinical data is received. The patient non-imaging clinical data may include a medical history of the patient (e.g., received from an EMR of the patient stored in EMR system 122), lab results of the patient, and patient monitoring/medical device data of the patient (e.g., received from one or more medical devices such one or more medical devices of the plurality of medical devices 124). Additional data may be included in the clinical data, such as prior and/or currently administered treatments and other interventions (when not included in the medical device data).

At 206, imaging features are derived from the imaging scan information and non-imaging features are derived from the clinical data. Additional details about the feature derivation/extraction process is provided below with respect to FIGS. 3 and 4. Briefly, the imaging scan information is pre-processed and supplied to one or more feature extractors, which may extract clinically- and model-relevant features from the medical images, such as relevant anatomical features, anatomical appearances (e.g., textures), imaging features (e.g., B-lines in ultrasound images), and the like. Likewise, the clinical data is pre-processed and supplied to one or more feature extractors, which may extract model-relevant features from the clinical data, such as signal envelopes, signal means, standard deviation, etc., parameter-specific features such as ECG QT intervals, heart rate, and the like.

At 208, the imaging features are input into an imaging model and the non-imaging features are input into a non-imaging model. The imaging model may be a machine learning/AI model trained to output respiratory support recommendations as a function of the imaging features, such as imaging model 108 of FIG. 1. For example, the imaging model may be a deep neural network and the imaging features (as output by the feature extractors as described below with respect to FIG. 3) may be entered into an input layer of the deep neural network and the imaging features may be mapped to an output using the deep neural network. Mapping the imaging features to the output may include inputting data from the imaging features into an input layer/input tile of the deep neural network, and propagating the input data through each layer of the deep neural network until the output is produced by an output layer of the deep neural network. In some embodiments, the deep neural network comprises a convolutional neural network.

The non-imaging model may be a machine learning/AI model trained to output respiratory support recommendations as a function of the non-imaging features, such as non-imaging model 110 of FIG. 1. In examples where the non-imaging model is a deep neural network, such as a convolutional neural network, the non-imaging features may be input into an input layer/input tile of the deep neural network and propagated through each layer of the deep neural network until the output is produced by an output layer of the deep neural network.

At 210, the imaging features and the non-imaging features are input into a joint model. The joint model may be a machine learning/AI model trained to output respiratory support recommendations as a function of the imaging features and the non-imaging features, such as joint model 112 of FIG. 1. In order to enter combined imaging and non-imaging features into the joint model, the imaging features and non-imaging features may be concatenated and/or the imaging features and non-imaging features may be embedded into a latent space using another neural network. In examples where the joint model is a deep neural network, the combined imaging and non-imaging features may be input into an input layer/input tile of the deep neural network and propagated through each layer of the deep neural network until the output is produced by an output layer of the deep neural network.

At 212, the output of the imaging model, the non-imaging model, and/or the joint model is displayed on a suitable display device (e.g., display device 118). The models may output two sets of outputs—a respiratory support mode output and a relevant settings output. The respiratory support mode output may include a recommendation for oxygen support, non-invasive ventilation, mechanical ventilation, or no respiratory support. Thus, the respiratory support mode output may include a recommendation to initiate, continue, or terminate one or more respiratory support modes (e.g., oxygen support, non-invasive ventilation, etc.). The relevant settings output may include recommended settings for a relevant respiratory support mode, such as FiO2 levels or PEEP levels, Tidal Volume, etc. The mode variables may be binary (e.g., each respiratory support mode may be given a yes/no recommendation) and the settings may be continuous. Further, the output may include labels and confidence scores.

In some examples, the output from each of the imaging model, the non-imaging model, and the joint model may be displayed. In other examples, only the output from the joint model may be displayed. Further, when imaging features are not available (e.g., no relevant medical images have been acquired for the patient), only the output from the non-imaging model may be displayed. In examples where the output from only the joint model (and not the imaging model and non-imaging model) is displayed, the output may be displayed along with a relative confidence level that the output is accurate. If the output from the various models (e.g., the joint model, the imaging model, and non-imaging model) is in agreement (e.g., each model outputs the same respiratory support mode and relevant settings), the confidence level may be higher. If there is disagreement among the models (e.g., the imaging model outputs a different respiratory support mode than the non-imaging model), the confidence level may be lower. In this way, if there is no agreement between the models, a low confidence for the predictions may be displayed and whether to follow the recommendations may be left to the discretion of the clinician. The degree of disagreement captures the confidence in recommendations—the lesser the agreement, the lower the confidence and vice versa.

Figure 6:
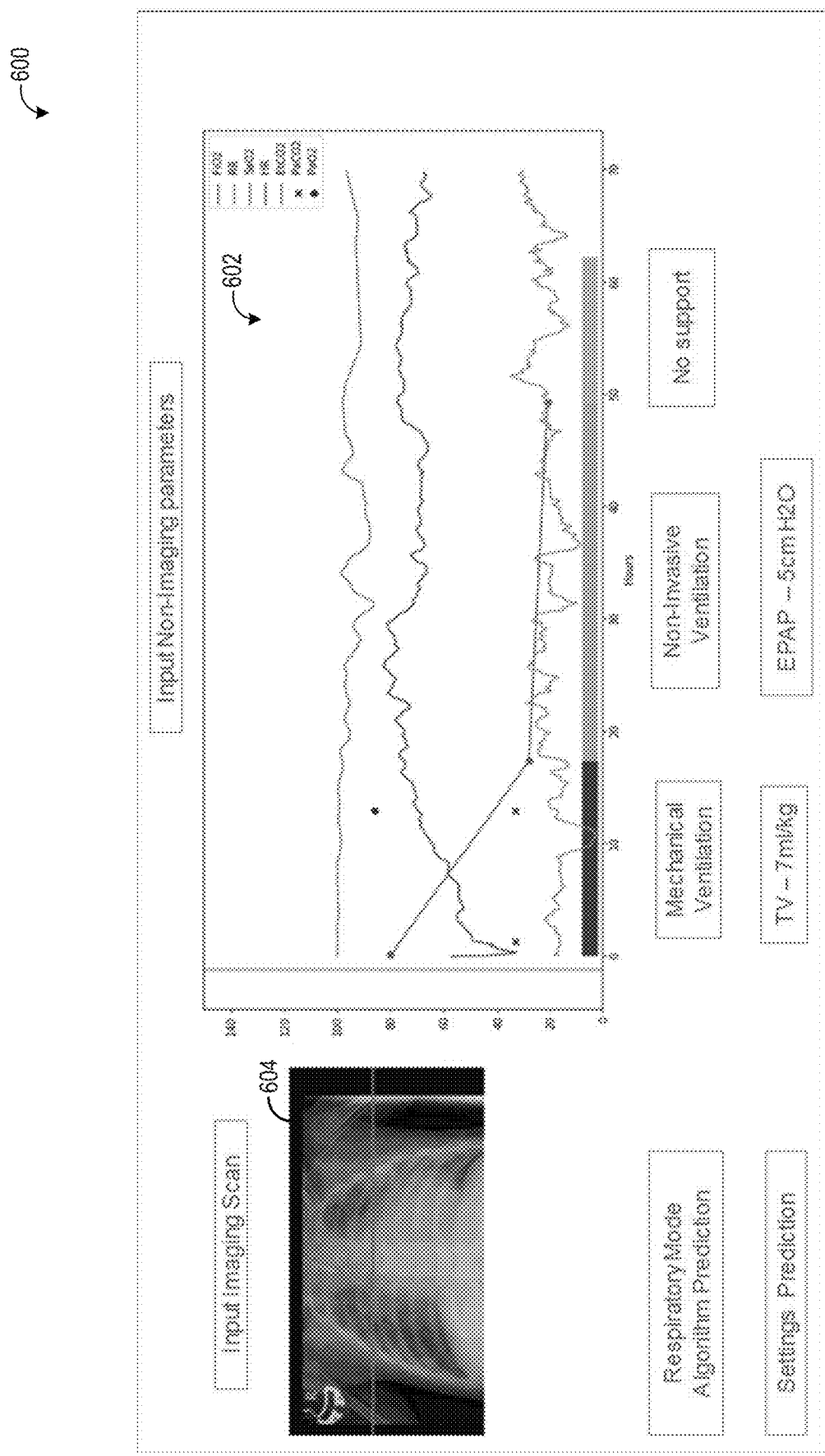
FIG. 6 is an example graphical user interface that may be output for display on a display device, including respiratory support recommendations generated according to the method of FIG. 2.

The output may be displayed as part of a patient-specific graphical user interface, such as the example interface shown in FIG. 6. In other examples, the output may be displayed on a text-based user interface (TUI). In other examples, the output may be displayed as part of a multi-patient dashboard, where the respiratory support status of a plurality of COVID-19 patients are displayed (e.g., on a display device at a nurses' station or other unit or ward-specific display device, or on a care provider device). By executing method 200 for a plurality of patients and then displaying the output recommendations for each patient in a single dashboard, clinician decisions about resource management and patient treatment may be informed and performed in an expedited manner, avoiding the need for clinicians to refer to individual patient records. Additionally, the output of the imaging model, non-imaging model, and joint model may be saved in memory. The output recommendations may be saved as part of the patient EMR, as a dashboard tracking patient status and recommendations, and/or as part of analytics data that may be used to train/update the models described herein as well as used by administrators or other authorities to guide treatment protocols and resource management.

In some examples, the contributing factors to the model output may be determined and displayed, as indicated at 214. For example, if a recent lung CT image showed improvement in patient condition and this lung CT image was deemed a contributing factor to the output of the joint model (e.g., recommending extubation of the patient), an indication that the lung CT was a contributing factor to the recommendation may be displayed along with the model output. The lung CT image may be deemed a contributing factor to the output of the joint model based on contribution weight values assigned by the models to each factor used, where a higher contribution weight value corresponds to a more significant contribution. Contribution weight values may be assigned to factors based on historical frequency of being included in model calculations, accuracy of model output when the factor is included in model calculations compared to accuracy of model output when the factor is not included, and the like. Further, to identify relevant factors from non-clinical data, specific model diagnostic tools may be utilized. For example, an entropy minimizer in gradient boosting/tree-based models may be used to identify features that contributed more to minimization of overall training loss. Post-inference, techniques such as shapely values that capture the expected marginal contribution from each feature may be utilized to identify the relevant/contributing factors. From the imaging data, techniques from the family of guided back-propagation may be used to highlight which region of the input image contributed towards a particular decision. Method 200 then ends.

Figure 3:
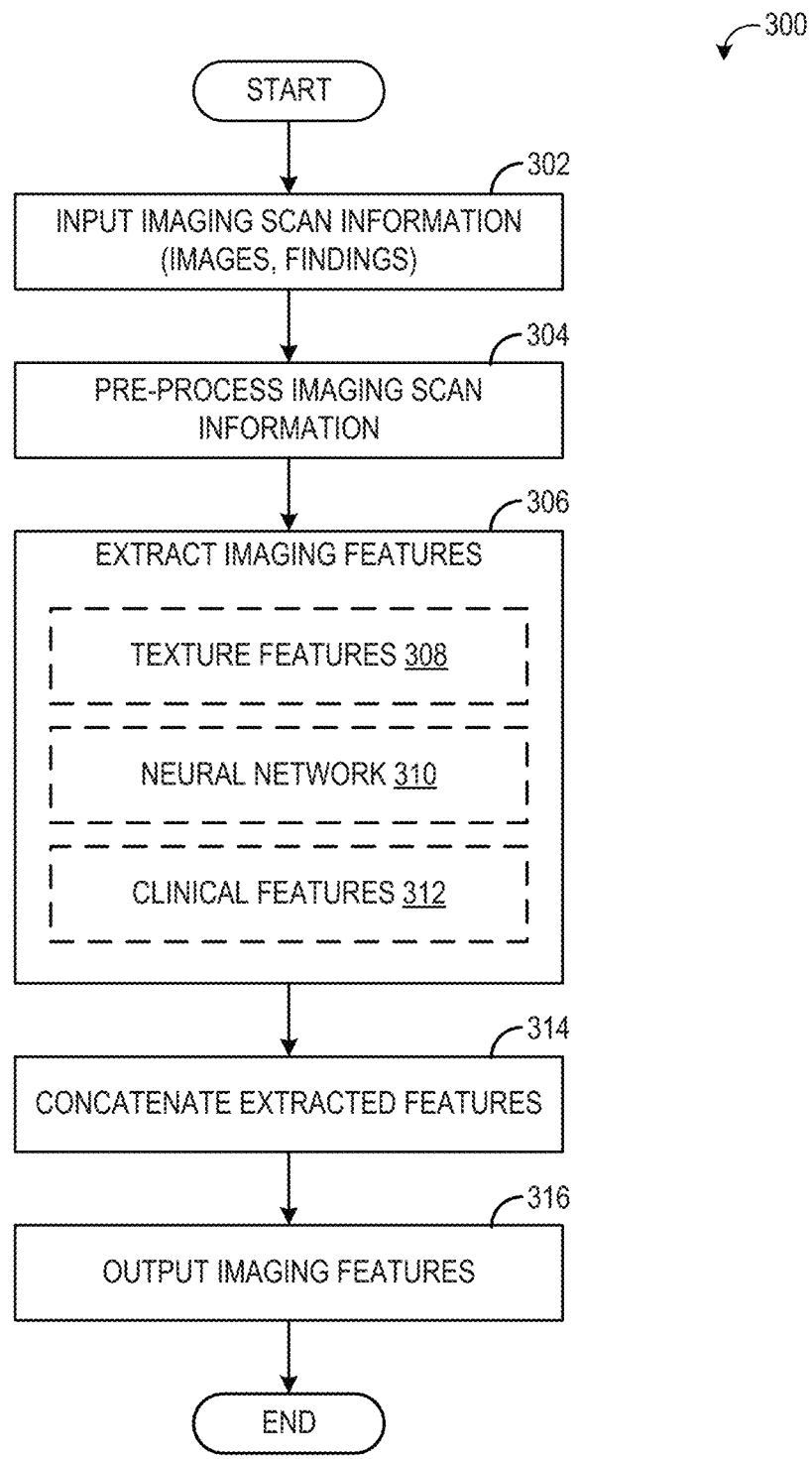
FIG. 3 is a flowchart illustrating a method for extracting imaging features from imaging data, for input to the support recommendation system in order to generate the respiratory support recommendations, according to an embodiment of the disclosure.

FIG. 3 is a flowchart illustrating a method 300 for extracting imaging features from patient imaging scan information. Method 300 may be carried out according to instructions stored in non-transitory memory of a computing device, such as support recommendation system 102. In some examples, method 300 may be carried out as part of method 200, for example in order to extract the imaging features that are input into the imaging model.

At 302, imaging scan information is input into an imaging feature extractor module. The imaging scan information may include medical/diagnostic images and, in some examples, clinician findings associated with the images. For example, the medical images may include lung CT images and the findings may include indications that the lungs include opaque lesions consistent with COVID-19. In other examples, the imaging scan information may only include the medical images.

At 304, the imaging scan information is pre-processed. The pre-processing may include field of view (FOV) normalization, size normalization (resizing and cropping), intensity normalization, and the like. Normalizations may include removing extra image data such as image data outside the FOV, so that consistently sized and positioned FOV image data may be provided to the model, to increase the accuracy of pre-processing imaging scan information. At 306, imaging features are extracted from the pre-processed imaging scan information. The pre-processed images may be passed through traditional computer vision modules, clinical features modules, as well as neural network modules. Extracting the imaging features may include extracting texture features, as indicated at 308. Examples of imaging texture features include histogram of gradients (HoG), scale invariant feature transform (SIFT), and wavelet decompositions. Extracting the imaging features may include extracting the imaging features via a neural network, as indicated at 310. Neural network features may be obtained from standard pre-trained architectures like VGGNet, etc., or using auto-encoder based architectures on the same data. Extracting the imaging features may include extracting clinical features, as indicated at 312. The clinical features may include scan-specific features such as the area of the affected region, bilateral signatures, opacity, or presence of B-lines in ultrasound images, etc. Further, in some examples, change in features in the images over time may be extracted, such as temporal changes in CT images, which may show progression of abnormalities and return to normalcy.

At 314, the extracted imaging features may be concatenated and the concatenated imaging features may be output at 316. The concatenated extracted imaging features may be entered as input to the imaging model and/or joint model, as explained with respect to FIG. 2, and/or used to train the imaging model and joint model. Method 300 then ends.

Figure 4:
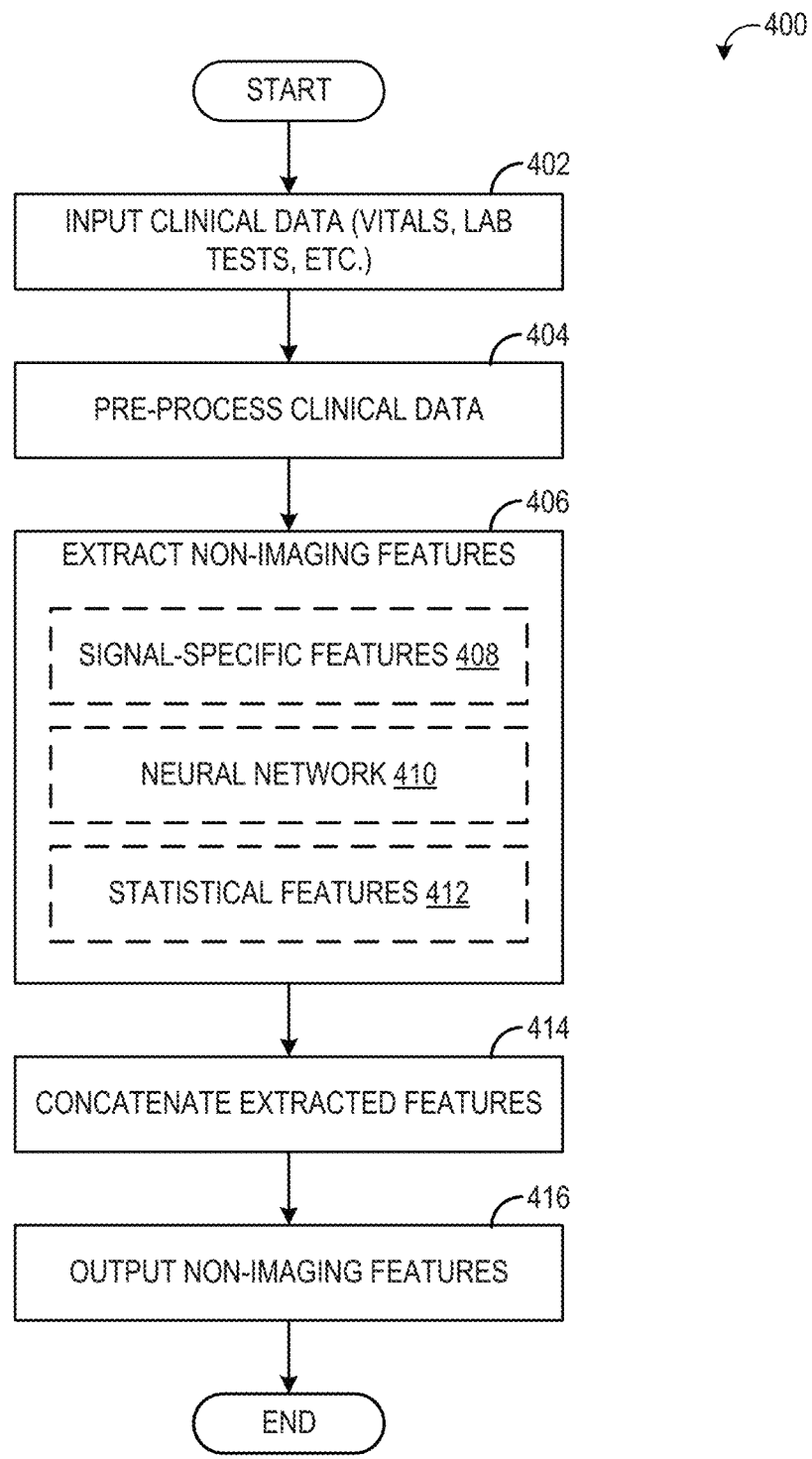
FIG. 4 is a flowchart illustrating a method for extracting non-imaging features from clinical data, for input to the support recommendation system in order to generate the respiratory support recommendations, according to an embodiment of the disclosure.

FIG. 4 is a flowchart illustrating a method 400 for extracting non-imaging features from patient clinical data. Method 400 may be carried out according to instructions stored in non-transitory memory of a computing device, such as support recommendation system 102. In some examples, method 400 may be carried out as part of method 200, for example in order to extract the non-imaging features that are input into the non-imaging model.

At 402, clinical data is input into a non-imaging feature extractor module. The clinical data may include vital signs, lab tests, interventions, patient history, etc. The vital signs may include measured or inferred physiological parameters, such as heart rate, blood oxygen saturation, respiration rate, etc. The vital signs may include time series data, e.g., a plurality of values over time. Further, the clinical data may include patient therapy device settings, when available.

At 404, the clinical data is pre-processed. The pre-processing may include noise removal and filtering, data imputation, scale normalization, and the like. Further, the pre-processing may include replacing missing signals with an average value, which may include indicator variables capturing presence or absence of signals. During pre-processing, samples may be collected over specific time-windows retrospectively (e.g., the past 3 hours of clinical data) and features may be extracted over the collected samples to be mapped to ground-truth recommendations. At 406, non-imaging features are extracted from the pre-processed clinical data. The pre-processed clinical data may be passed through signal-specific features modules, statistical modules, as well as the neural network modules. Extracting the non-imaging features may include extracting signal-specific features, as indicated at 408. Examples of signal-specific features may include features extracted on electrocardiograms (ECG)—QT intervals, PR intervals, heart rate, etc. Extracting the non-imaging features may include extracting the non-imaging features via a neural network, as indicated at 410. Neural network features may be obtained using auto-encoder based architectures on the same data or transferred from related problems. Extracting the non-imaging features may include extracting statistical features, as indicated at 412. The statistical features may include averages like mean, standard deviation, and higher order moments, short-term and long-term averages computed over varying time windows, etc.

At 414, the extracted non-imaging features may be concatenated and the concatenated non-imaging features may be output at 416. The concatenated extracted non-imaging features may be entered as input to the non-imaging model and/or joint model, as explained with respect to FIG. 2, and/or used to train the non-imaging model and joint model. Method 400 then ends.

Figure 5:
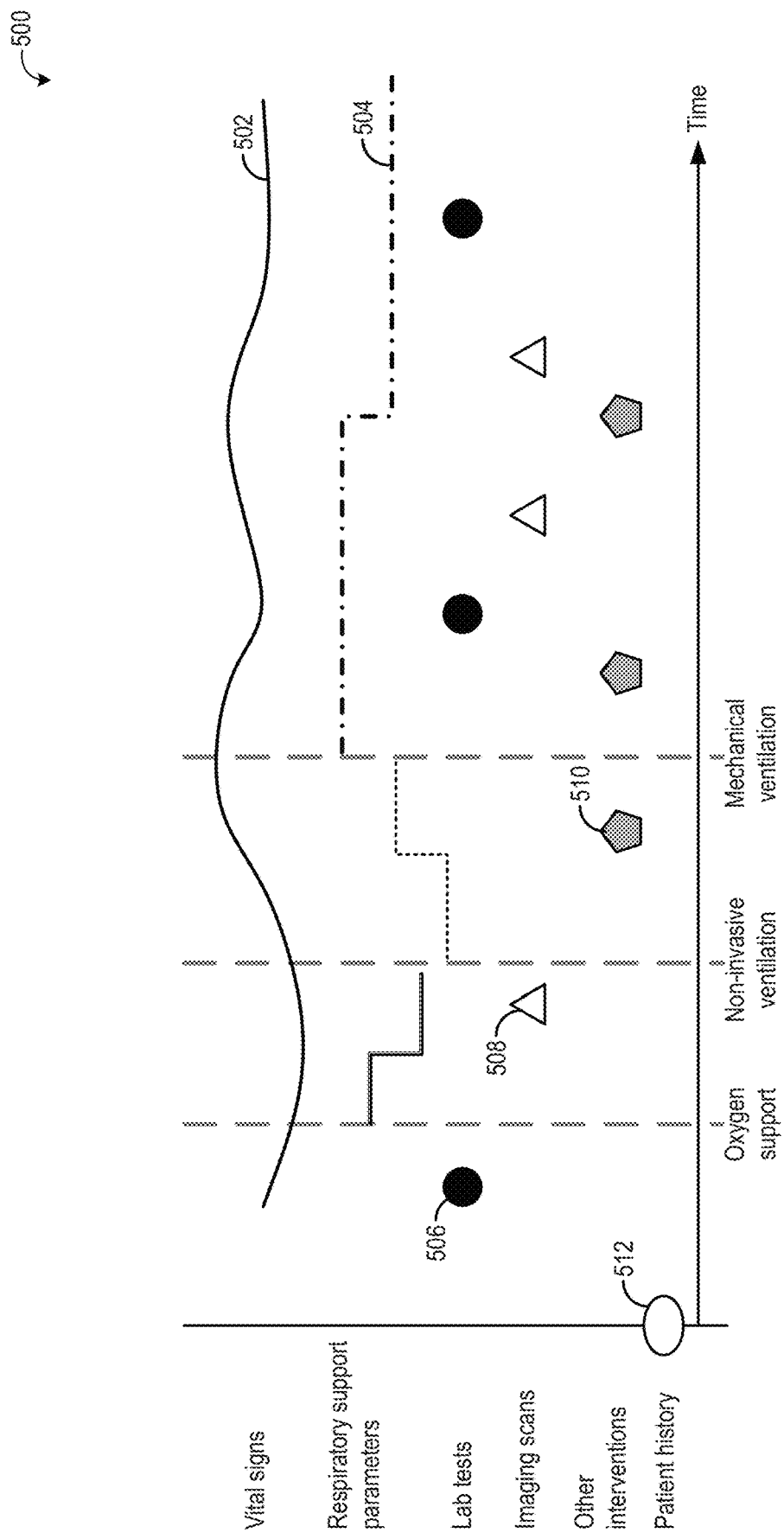
FIG. 5 is a timeline showing example imaging and non-imaging data for a patient that may be collected and used as input to the support recommendation system for generating respiratory support recommendations, according to an embodiment of the disclosure.

FIG. 5 shows an example timeline 500 of patient data and events over the course of a patient stay in a medical facility, where the patient has a suspected or diagnosed COVID-19 status. Timeline 500 includes example patient vital signs, shown by curve 502, respiratory support parameters, shown by curve 504, lab testing events, shown by the black circles (e.g., lab test 506), imaging scans, shown by white triangles (e.g., imaging scan 508), other interventions, shown by grey pentagons (e.g., intervention 510), and patient history ascertainment (show by patient history 512), each plotted as a function of time.

As appreciated by timeline 500, when the patient is admitted to the medical facility, the patient history 512 is obtained upon admission. Thereafter, vital signs of the patient begin being monitored. The vital signs may include respiratory rate, SpO2, and heart rate, though other vital signs/medical data are possible. The vital signs may be measured or inferred continuously or periodically at a suitable frequency (e.g., once a second, once a minute, etc.) but are understood to be measured or inferred at a relatively high frequency. Curve 502 shows an example plot of a vital sign (e.g., SpO2) that may be obtained by plotting measuring or inferred values over time, and it is to be appreciated that each vital sign/medical data that is measured or inferred for the patient may have its own waveform/time series of data.

A lab test may be received, such as lab test 506, at which point the patient may be placed on oxygen support. Once on oxygen support, oxygen support parameters may be received, indicating oxygen concentration, flow rate, and the like. While on oxygen support, an imaging scan of the patient may be obtained, such as imaging scan 508. As the patient condition changes or fails to improve, the patient is placed on non-invasive ventilation, and thus the respiratory support parameters that are received switch from oxygen support parameters to non-invasive ventilation parameters, which may further include the pressure of the supplied air/oxygen, the ventilation rate, and so forth. While on non-invasive ventilation, another type of intervention may be performed on the patient, as shown by intervention 510. The intervention may include proning or another intervention. As the patient condition changes or fails to improve, the patient is placed on invasive ventilation, and thus the respiratory support parameters that are received switch from non-invasive ventilation parameters to ventilator parameters, which may include minute volume (MV), fraction of intake oxygen (FiO2), positive end expiratory pressure (PEEP), end tidal carbon dioxide (EtCO2), peak inspiratory pressure (PIP), tidal volume (TV), etc.

While ventilated, lab tests may be received, additional interventions may be performed, and additional imaging scans may be performed. When the imaging and non-imaging data shown and described with respect to FIG. 5 are entered into the imaging model, non-imaging model, and joint model as described herein, recommendations may be made that may guide the clinical decisions shown in FIG. 5. For example, the lab test 506 and vital signs may be entered as non-imaging data to the non-imaging model, which may recommend oxygen support. Once the imaging scan 508 is performed, the acquired medical images may be entered into the imaging model, and the medical images and the non-imaging data (e.g., the vital signs and the lab test results) may be entered into the joint model, which may recommend the patient be placed on the non-invasive ventilation. As another example, as the additional imaging scans are performed, lab test results are received, and vital signs are collected as the patient is ventilated with the invasive ventilator, the imaging and non-imaging data may be input into the joint model, which may output recommendations as to the ventilator machine settings.

In this way, the approach described herein may integrative and longitudinal, as multiple, different types of data may be integrated to achieve the recommendations as described herein. Further, the data may be input to the model(s) at a suitable frequency over time, with new data added as input when available. This may provide changing recommendations as patient condition changes. Further, the imaging scan information may be used over time to guide treatment decisions, such as ventilator machine settings, whether or not to intubate or extubate, etc., which may make the recommendations more robust and/or increase a confidence of the recommendations (e.g., relative to relying only on the non-imaging data).

Thus, embodiments are disclosed herein for a system to continuously monitor and predict ventilation needs of COVID-19 subjects or subject suffering from other respiratory conditions using integrated longitudinal AI analysis of imaging and non-imaging biomarkers by receiving one or more imaging scans across different time-points of hospital stay, receiving non-imaging clinical parameters continuously during hospital stay, using AI/machine learning (ML) methods to derive features and models from longitudinal imaging scans, using AI/ML methods to derive features and models from non-imaging parameters, and using combiner AI modules to fuse features and scores from individual and joint models to predict intubation, extubation, and different modes of respiratory support and settings of invasive/non-invasive ventilation and oxygen support. This may include displaying "contributing" factors for decision adding interpretability. The AI/ML methods may include conventional machine learning methods like boosted trees or multi-modal neural network architectures to fuse imaging and non-imaging biomarkers. With respect to the combiner AI modules, one example combiner that may be applied is decision combiners, where results from the two models are averaged. For example, the imaging model will give certain likelihoods for different respiratory support options and the non-imaging model will also provide its own likelihoods. The outputs from the two models may be averaged and presented to the end user. This will reduce the erroneous predictions from either of the models and provide a more stable prediction. As another example, another machine learning model may be trained, which will work on predictions from the two models and may be optimized during training to match ground-truth oxygen support recommendations. During inference, this model may be deployed to combine the inferences from the imaging and non-imaging models.

FIG. 6 shows an example graphical user interface (GUI) 600 that may be output for display on a display device (e.g., display device 118) in order to visualize the output of the support recommendation models described herein. For example, GUI 600 may be displayed as part of method 200 described above. GUI 600 includes a plot 602 of clinical data over time. The plot 602 includes FiO2, respiratory rate (RR), SpO2, heart rate (HR), EtCO2, PaCO2, and PaO2, though other pieces of patient medical data are possible. GUI 600 also includes an example medical image 604. The clinical/medical device data shown in plot 602 as well as the medical image 604 (and other medical images) may be input to the imaging model, non-imaging model, and/or joint model as described above with respect to FIG. 2. The model(s) may output respiratory support recommendations, which are displayed as part of GUI 600. For example, as shown, the outputs may include a respiratory mode prediction and a settings prediction.

GUI 600 shows a progression of outputs made over time, which time-align with the plot 602. For example, the model(s) may recommend mechanical ventilation from time 0-18 hours, with a TV setting of 7 ml/kg. The model(s) may recommend non-invasive ventilation from time 18-49 hours, with an expiratory positive airway pressure (EPAP) setting of 5 cm H2O. At time 49 hours, the model(s) may recommend no respiratory support. In some examples, the example medical image displayed in GUI 600 (e.g., medical image 604) may be an image that was deemed a contributing factor to the latest recommendation, e.g., the image may show lessened symptoms of COVID thus precipitating the recommendation to remove the patient from respiratory support.

The technical effect of entering both imaging and non-imaging features of patient medical data to one or more models trained to output respiratory support recommendations is that more robust recommendations with higher confidence may be generated, which may guide clinicians to make patient care decisions in situations where established protocols are not widely available, such as during outbreaks of COVID-19.

The disclosure also provides support for a method, comprising: extracting imaging features from patient imaging information for a patient, extracting non-imaging features from patient clinical data of the patient, entering the imaging features and the non-imaging features to a joint model trained to output respiratory support recommendations as a function of the imaging features and the non-imaging features, and displaying one or more respiratory support recommendations output by the joint model. In a first example of the method, the method further comprises: entering the imaging features to an imaging model trained to output respiratory support recommendations as a function of the imaging features, and wherein displaying one or more respiratory support recommendations output by the joint model comprises displaying one or more respiratory support recommendations output by the joint model and the imaging model. In a second example of the method, optionally including the first example, the method further comprises: entering the non-imaging features to a non-imaging model trained to output respiratory support recommendations as a function of the non-imaging features, and wherein displaying one or more respiratory support recommendations output by the joint model comprises displaying one or more respiratory support recommendations output by the joint model and the non-imaging model. In a third example of the method, optionally including one or both of the first and second examples, the one or more respiratory support recommendations output by the joint model comprise a recommendation to initiate, continue, or terminate a respiratory support mode. In a fourth example of the method, optionally including one or more or each of the first through third examples, the respiratory support mode comprises oxygen support, non-invasive ventilation, or invasive ventilation. In a fifth example of the method, optionally including one or more or each of the first through fourth examples, the one or more respiratory support recommendations output by the joint model further comprise one or more recommended settings for the respiratory support mode. In a sixth example of the method, optionally including one or more or each of the first through fifth examples, the joint model is machine learning model. In a seventh example of the method, optionally including one or more or each of the first through sixth examples, the joint model is a neural network trained to output the one or more respiratory support recommendations as a function of the imaging features and the non-imaging features. In an eighth example of the method, optionally including one or more or each of the first through seventh examples, the neural network is trained with training data including training imaging features and training non-imaging features for a plurality of patients and ground truth for the plurality of patients, where each patient in the plurality of patients received a suspected or confirmed diagnosis of COVID-19. In a ninth example of the method, optionally including one or more or each of the first through eighth examples, the patient imaging information comprises one or more medical images of the patient. In a tenth example of the method, optionally including one or more or each of the first through ninth examples, the patient clinical data includes a patient history of the patient, measured or inferred medical device data of the patient, and/or lab test results of the patient.

The disclosure also provides support for a system comprising: a memory storing a trained deep neural network and a plurality of feature extraction modules, and a processor communicably coupled to the memory and configured to: extract imaging features from patient imaging information for a patient via one or more feature extraction modules of the plurality of feature extraction modules, extract non-imaging features from patient clinical data of the patient via one or more feature extraction modules of the plurality of feature extraction modules, map the imaging features and the non-imaging features to one or more outputs using the trained deep neural network, and output the one or more outputs for display on a display device, where the one or more outputs include one or more respiratory support recommendations for the patient. In a first example of the system, extracting imaging features from the patient imaging information comprises extracting one or more of anatomical features in the patient imaging information, texture features in the patient imaging information, and clinical features in the patient imaging information. In a second example of the system, optionally including the first example, the clinical features include one or more of an area of a selected anatomical region, bilateral signatures, opacity, and presence of B-lines in the patient imaging information. In a third example of the system, optionally including one or both of the first and second examples, the patient clinical data includes a patient history of the patient, measured or inferred medical device data of the patient, and/or lab test results of the patient. In a fourth example of the system, optionally including one or more or each of the first through third examples, extracting non-imaging features from the patient clinical data comprises extracting signal-specific features and/or statistical features from the measured or inferred medical device data. In a fifth example of the system, optionally including one or more or each of the first through fourth examples, the one or more respiratory support recommendations comprise a recommendation to initiate, continue, or terminate a respiratory support mode. In a sixth example of the system, optionally including one or more or each of the first through fifth examples, the respiratory support mode comprises oxygen support, non-invasive ventilation, or invasive ventilation. In a seventh example of the system, optionally including one or more or each of the first through sixth examples, the one or more respiratory support recommendations further comprise one or more recommended settings for the respiratory support mode.

The disclosure also provides support for a system comprising: a memory storing a trained deep neural network, and a processor communicably coupled to the memory and configured to: extract imaging features from one or more medical images of a patient, extract non-imaging features from patient clinical data of the patient, enter the imaging features and the non-imaging features to the trained deep neural network, the trained deep neural network trained to output respiratory support recommendations as a function of the imaging features and the non-imaging features, display one or more respiratory support recommendations output by the trained deep neural network, and display an indication of which one or imaging features of the imaging features and/or which one or more non-imaging features of the non-imaging features contributed to the one or more respiratory support recommendations.

One or more specific embodiments of the present disclosure are described above in order to provide a thorough understanding. These described embodiments are only examples of systems and methods for generating respiratory support recommendations using machine learning/AI models. The skilled artisan will understand that specific details described in the embodiments can be modified when being placed into practice without deviating the spirit of the present disclosure.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object.

In addition, it should be understood that references to "one embodiment" or "an embodiment" of the present disclosure are not intended to be interpreted as excluding the existence of additional embodiments that also incorporate the recited features. In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method executable by a support recommendation system including a processor configured to execute machine readable instructions stored in non-transitory memory, comprising:

obtaining patient imaging information for a patient from a picture archive and communication system;

extracting, via the support recommendation system, imaging features from the patient imaging information, the imaging features including one or more of anatomical features in the patient imaging information, texture features in the patient imaging information, and clinical features in the patient imaging information;

entering, via the support recommendation system, the imaging features as input to an imaging model trained to output a first respiratory support recommendation based on the imaging features, the imaging model trained with first training data pairs each comprising a respective medical image of a respective patient and corresponding first ground truth data for that patient, the first ground truth data including expert annotations of clinical findings, prior and/or subsequent respiratory support administered to that patient, and outcomes of that patient;

obtaining patient clinical data of the patient from an electronic medical record system and/or one or more medical devices;

extracting, via the support recommendation system, non-imaging features from the patient clinical data, the non-imaging features including signal-specific features and statistical features from measured or inferred medical device data of the patient, the statistical features including mean, standard deviation, and/or higher order moments, and/or short-term and/or long-term averages computed over varying time windows;

entering, via the support recommendation system, the non-imaging features as input to a non-imaging model trained to output a second respiratory support recommendation based on the non-imaging features, the non-imaging model trained with second training data pairs each comprising clinical data of a respective patient and corresponding second ground truth data for that patient, the second ground truth data including expert annotations of prior and/or subsequent respiratory support administered to that patient and outcomes of that patient;

entering, via the support recommendation system, the imaging features and the non-imaging features to a joint model trained to output a third respiratory support recommendation as a function of the imaging features and the non-imaging features, wherein the joint model is a machine learning model trained with training data including training imaging features and training non-imaging features for a plurality of patients and ground truth for the plurality of patients;

displaying at least the third respiratory support recommendation and a confidence level of the third respiratory support recommendation, the confidence level determined via the support recommendation system based on a level of agreement among the first, second, and third respiratory support recommendations, wherein each respiratory support recommendation comprises a recommendation for a respiratory support mode selected from a plurality of possible respiratory support modes, the plurality of possible respiratory support modes including oxygen support, non-invasive ventilation, mechanical ventilation, and no respiratory support;

obtaining new patient imaging information and new patient clinical data for the patient, wherein the new patient clinical data includes prior and/or currently administered treatments for the patient;

mapping imaging features and non-imaging features from the new patient imaging information and the new patient clinical data, including the prior and/or currently administered treatments for the patient, to a fourth respiratory support recommendation using the joint model; and displaying the fourth respiratory support recommendation.

2. The method of claim 1, wherein displaying at least the third respiratory support recommendation comprises displaying each of the first, second, and third respiratory support recommendations.

3. The method of claim 1, wherein the joint model further outputs one or more recommended settings for the respiratory support mode.

4. The method of claim 1, wherein the joint model is a neural network.

5. The method of claim 4, wherein each patient in the plurality of patients received a suspected or confirmed diagnosis of COVID-19.

6. The method of claim 1, wherein the patient imaging information comprises one or more medical images of the patient.

7. The method of claim 1, wherein the patient clinical data includes a patient history of the patient, measured or inferred medical device data of the patient, and/or lab test results of the patient.

8. A system comprising:
a memory storing a trained deep neural network and a plurality of feature extraction modules; and
a processor communicably coupled to the memory and configured to:
extract imaging features from patient imaging information for a patient via one or more feature extraction modules of the plurality of feature extraction modules, the extracted imaging features including one or more of anatomical features in the patient imaging information, texture features in the patient imaging information, and clinical features in the patient imaging information;

extract non-imaging features from patient clinical data of the patient via one or more feature extraction modules of the plurality of feature extraction modules, the extracted non-imaging features including signal-specific features and statistical features from measured or inferred medical device data of the patient, the statistical features including mean, standard deviation, and/or higher order moments, and/or short-term and/or long-term averages computed over varying time windows;

map the imaging features and the non-imaging features to one or more outputs using the trained deep neural network, including concatenating the imaging features and the non-imaging features and entering the concatenated imaging features and non-imaging features as input to the trained deep neural network, the trained deep neural network trained to generate the one or more outputs for patients having a given condition;

output the one or more outputs for display on a display device, where the one or more outputs include one or more respiratory support recommendations for the patient, the one or more respiratory support recommendations including a recommendation for a respiratory support mode selected from a plurality of possible respiratory support modes, the plurality of possible respiratory support modes including oxygen support, non-invasive ventilation, mechanical ventilation, and no respiratory support;

receive new patient imaging information and new patient non-imaging information for the patient, wherein the new patient non-imaging information includes prior and/or currently administered treatments for the patient;

map imaging features and non-imaging features from the new patient imaging information and the new patient non-imaging information, including the prior and/or currently administered treatments for the patient, to one or more further outputs using the trained deep neural network; and output the one or more further outputs for display on the display device.

9. The system of claim 8, wherein the given condition is COVID-19.

10. The system of claim 8, wherein the clinical features include one or more of an area of a selected anatomical region, bilateral signatures, opacity, and presence of B-lines in the patient imaging information.

11. The system of claim 8, wherein the patient clinical data further includes a patient history of the patient and/or lab test results of the patient.

12. The system of claim 8, wherein the one or more respiratory support recommendations further comprise one or more recommended settings for the respiratory support mode.

13. A system comprising:
a memory storing a trained deep neural network trained with ground truth respiratory support recommendations; and
a processor communicably coupled to the memory and configured to:
extract imaging features from one or more medical images of a patient, the imaging features including one or more of anatomical features in the one or more medical images, texture features in the one or more medical images, and clinical features in the one or more medical images;

enter the imaging features as input to an imaging model trained to output a first respiratory support recommendation based on the imaging features, the imaging model trained with first training data pairs each comprising a respective medical image of a respective patient and corresponding first ground truth data for that patient, the first ground truth data including expert annotations of clinical findings, prior and/or subsequent respiratory support administered to that patient, and outcomes of that patient;

extract non-imaging features from patient clinical data of the patient, the non-imaging features including signal-specific features and statistical features from measured or inferred medical device data of the patient, the statistical features including mean, standard deviation, and/or higher order moments, and/or short-term and/or long-term averages computed over varying time windows;

enter the non-imaging features as input to a non-imaging model trained to output a second respiratory support recommendation based on the non-imaging features, the non-imaging model trained with second training data pairs each comprising clinical data of a respective patient and corresponding second ground truth data for that patient, the second ground truth data including expert annotations of prior and/or subsequent respiratory support administered to that patient and outcomes of that patient;

enter the first respiratory support recommendation and the second respiratory support recommendation to the trained deep neural network, the trained deep neural network trained to output a final respiratory support recommendation as a function of the first respiratory support recommendation and the second respiratory support recommendation;

display the final respiratory support recommendation output by the trained deep neural network;

display an indication of which one or more imaging features of the imaging features and/or which one or more non-imaging features of the non-imaging features contributed to the first, second, and/or final respiratory support recommendation;

obtain new patient medical images and new patient clinical data for the patient, wherein the new patient clinical data includes prior and/or currently administered treatments for the patient;

map imaging features from the new patient medical images to a third respiratory support recommendation using the imaging model and map non-imaging features from the new patient clinical data, including the prior and/or currently administered treatments for the patient, to a fourth respiratory support recommendation using the non-imaging model;

enter the third respiratory support recommendation and the fourth respiratory support recommendation to the trained deep neural network to obtain an updated final respiratory support recommendation; and display the updated final respiratory support recommendation.

\* \* \* \* \*